United States Patent [19]

Inoue et al.

[11] Patent Number: 5,610,170
[45] Date of Patent: Mar. 11, 1997

[54] PACKAGE FORM FOR BICARBONATE-CONTAINING POWDERY PHARMACEUTICAL COMPOSITIONS AND A METHOD OF STABILIZING THE COMPOSITIONS

[75] Inventors: Fujio Inoue; Masamitsu Izumi, both of Naruto; Satoru Hayashi, Tokushima-ken, all of Japan

[73] Assignee: Otsuka Pharmaceutical Factory, Inc., Tokushima-ken, Japan

[21] Appl. No.: 307,804

[22] PCT Filed: Jan. 14, 1994

[86] PCT No.: PCT/JP94/00041

§ 371 Date: Mar. 14, 1995

§ 102(e) Date: Mar. 14, 1995

[87] PCT Pub. No.: WO94/16663

PCT Pub. Date: Aug. 4, 1994

[30] Foreign Application Priority Data

Jan. 22, 1993 [JP] Japan ................... 5-009419

[51] Int. Cl.⁶ ........................... A61J 1/00
[52] U.S. Cl. ........................... 514/340; 604/416
[58] Field of Search ............. 514/340; 604/403, 604/416

[56] References Cited

FOREIGN PATENT DOCUMENTS

0067420A1 12/1982 European Pat. Off. .
6105905 4/1994 Japan .................. A61M 1/14

*Primary Examiner*—John C. Bleutge
*Assistant Examiner*—Robert H. Harrison
*Attorney, Agent, or Firm*—Sughrue, Mion, Zinn, Macpeak & Seas

[57] ABSTRACT

The invention provides a method and a package form for insuring a stabilized bicarbonate-containing pharmaceutical composition, the method comprises filling the bicarbonate-containing powdery pharmaceutical composition in a moisture- and gas-permeable plastic container, wrapping the so-filled container in a moisture- and gas-impermeable plastic wrapper and carrying out at least one procedure selected from the group consisting of the procedure of introducing a carbon dioxide gas into a space between the container and wrapper, the procedure of disposing a carbon dioxide-liberating deoxygenating agent in the space and the procedure of disposing a desiccant previously saturated with carbon dioxide gas by way of adsorption in the space. In accordance with the invention, the inherent objects of incorporating the bicarbonate can be accomplished without inducing the aging and degradation of the bicarbonate-containing powdery pharmaceutical composition.

9 Claims, 1 Drawing Sheet

PACKAGE FORM FOR BICARBONATE-CONTAINING POWDERY PHARMACEUTICAL COMPOSITIONS AND A METHOD OF STABILIZING THE COMPOSITIONS

TECHNICAL FIELD

The present invention relates to a method of stabilizing a bicarbonate-containing powdery pharmaceutical composition, particularly a novel method of stabilizing a bicarbonate-containing powdery pharmaceutical composition which allows the composition in a plastic container to remain wholesome without aging or degradation and the object of addition of the carbonate to be accomplished without compromise and to a package form for such bicarbonate-containing powdery pharmaceutical composition.

BACKGROUND ART

With very few exceptions such as sodium chloride, drugs are susceptible to aging loads such as water, oxygen and light and glass ampules have been in use for their storage since many years ago. However, with the recent advances in pharmaceutical science, material engineering, production methodology, production equipment, etc., these pharmaceutical containers are being replaced by glass vials and plastic (such as polyolefins, e.g. polyethylene, polypropylene, etc., ethylene-vinyl acetate copolymer, polyethylene terephthalate, polyvinyl chloride, etc.) containers which are easy for those engaged in medical practice to handle and easy to dispose of after use and the utilization of such plastic containers, in particular, is rapidly spreading of late.

However, unlike glass, plastics are inherently permeable to gas and moisture and have the disadvantage that containers made thereof cannot be used for all kinds of drugs. Recently, materials which are almost as impervious to gas and moisture as glass, such as a laminate film carrying a vapor-deposited aluminum layer or an aluminum foil, a laminate film carrying a vapor-deposited silicon monoxide layer, a multi-layer film consisting of plural materials such as polyethylene terephthalate, polyvinyl alcohol, polyvinylidene chloride, ethylene-vinyl alcohol copolymer, etc. have been developed and today plastics with an oxygen permeability rate of not more than 1.0 cc/m²·24 hrs/1 atm. and a moisture permeability rate of not more than 1.0 g/m²·24 hrs/1 atm. are available on the market and finding ever broadening usage and application.

Meanwhile, drugs are generally stable in the bulk form but if they are dissolved and administered to patients, the low pH values of the solutions would not only damage the local tissue at the administration site but also induce systemic disturbances or result in poor absorption. Therefore, a variety of pharmaceutical contrivances has so far been made to avoid the troubles. By way of illustration, assuming that the pharmaceutical composition contains a strongly acidic powdery substance such as the hydrochloride or an acidic powdery drug whose neutral salt would be unstable, it is common practice to formulate the drug with a bicarbonate to insure the proper pH on dissolution or convert it to the neutral salt which is more readily absorbed at the time of administration.

Moreover, drugs which are unstable in solution, for example certain antibiotics, are supplied in the powdery form but since these drugs in general are sparingly soluble in aqueous vehicles, a bicarbonate as a source of carbon dioxide gas, which assists in dissolution, is added as a solubilizer.

On the other hand, sodium hydrogen carbonate is contained as an alkalizing agent in dialysis fluid compositions for artificial kidney use and for the purpose of insuring the ease of handling and reducing the cost of shipment, the recent tread is toward converting such liquid compositions to powdery or granular preparations (e.g. Japanese Patent Application Kokai H3-38527 and Kokai H3-74331).

The bicarbonate contained in such pharmaceutical compositions liberates water and carbon dioxide gas with time but it is well known that in a closed system there is established an equilibrium among the bicarbonate, carbonate, water and carbon dioxide as indicated by the following relation (1).

$$2HCO_3^- \rightleftharpoons CO_3^{2-} + H_2O + CO_2 \qquad (1)$$

However, when a bicarbonate-containing powdery pharmaceutical composition is supplied in a plastic (such as polyolefins, e.g. polyethylene, polypropylene, etc., ethylene-vinyl acetate copolymer, polyvinyl chloride, etc.) container, the carbon dioxide gas and water liberated from the bicarbonate find their way out through the plastic container which is permeable to gas and moisture. As a result, the balance of the above relation (1) is tipped to the right to yield the carbonate so that when the composition is dissolved for administration, the intrinsic objects of adding the bicarbonate, namely supply of $HCO_3^-$, neutralization of the drug, and assistance in dissolution, cannot be accomplished. Moreover, the solution after reconstitution undergoes increase of pH to affect the stability of the drug solution. For the protection of a powdery pharmaceutical composition containing a drug liable to decompose on absorption of moisture and a bicarbonate, as supplied in a plastic container, from the decomposition due to moisture, it might be contemplated to dispose a desiccant externally of the plastic container and wrapping the plastic container and desiccant together in a wrapping material with proven performance qualities, e.g. an oxygen permeability rate of not more than 1.0 cc/m²·24 hrs/1 atm. and a water permeability rate of not more than 1.0 g/m²·24 hrs/1 atm., such as a laminate film carrying a vapor-deposited silicon oxide layer, a composite laminate film comprising a plurality of materials such as polyethylene terephthalate, polyvinyl alcohol, polyvinylidene chloride, ethylene-vinyl alcohol copolymer, etc. or a laminate film having a vapor-deposited aluminum layer or an aluminum foil which is equivalent to glass in barrier performance. In such cases, there still occur events similar to those encountered when a bicarbonate-containing powdery composition is simply filled into a plastic container. Thus, the water and carbon dioxide gas liberated from the bicarbonate are adsorbed on the included desiccant so that the balance of said relation (1) is tipped to the right to cause the formation of carbonate and, hence, an elevation of pH of the solution after reconstitution.

The present invention provides a new technology which overcomes all the above-mentioned problems associated with the provision of a bicarbonate-containing powdery pharmaceutical preparation in a plastic container which is permeable to moisture and gas by insuring an increased carbon dioxide concentration in the container, allowing the moisture to be dissipated to the extent not affecting the quality of the drug, and inhibiting decomposition of the bicarbonate and formation of the carbonate to suppress the increase of pH after reconstitution and allow the inherent objects of incorporation of the carbonate, namely supply of $HCO_3^-$, neutralization of the drug and assistance in dissolution, to be accomplished without compromise.

DISCLOSURE OF INVENTION

In accordance with the present invention there is provided a method of stabilizing a bicarbonate-containing powdery composition characterized in that the placement of a bicarbonate-containing powdery pharmaceutical composition in a plastic container permeable to moisture and gas is followed by at least one procedure selected from among the procedure of introducing carbon dioxide gas into a space between the container and a wrapper and the procedure of disposing a carbon dioxide-liberating deoxygenating agent in said space and the procedure of disposing a desiccant previously saturated with carbon dioxide gas by way of adsorption, particularly such a method of stabilizing a bicarbonate-containing powdery pharmaceutical composition for dialysis.

The present invention further provides the above stabilizing method wherein not only a carbon dioxide-liberating deoxygenating agent but also a desiccant is disposed in said space between the container and wrapper, which is applicable with particular advantage to the case in which said bicarbonate-containing powdery pharmaceutical composition is an antibiotic-containing composition.

The invention further provides a method of stabilizing a bicarbonate-containing powdery pharmaceutical composition characterized by filling the bicarbonate-containing powdery composition into a plastic container which is impermeable to moisture and gas and introducing carbon dioxide gas into said container, which method is applicable with particular advantage to the case in which said bicarbonate-containing powdery pharmaceutical composition is a powdered dialysate.

Furthermore, the present invention provides a package form contributory to the stabilization of a bicarbonate-containing powdery pharmaceutical composition which comprises a plastic container permeable to moisture and gas and adapted to contain the bicarbonate-containing powdery pharmaceutical composition and a plastic packaging wrapper as implemented by following at least one procedure selected from the group consisting of the procedure of filling the space between said container and wrapper with carbon dioxide gas, the procedure of disposing a carbon dioxide gas-liberating deoxygenating agent in said space and the procedure of disposing a desiccant saturated with carbon dioxide gas by way of adsorption in said space.

The moisture- and gas-permeable plastic container used for accommodating a bicarbonate-containing powdery pharmaceutical composition for the use of the present invention may be made of various materials which are permeable to moisture and gas including but not limited to polyolefins such as polyethylene, poly-propylene, ethylene-α-olefin copolymers, etc., ethylene-vinyl acetate copolymer, polyvinyl chloride, polyamides, etc., inclusive of multi-layer films comprising such materials in various combinations.

The moisture- and gas-impermeable plastic wrapper for use in the present invention includes, among others, moisture- and gas-impermeable aluminum-laminated films, laminate films carrying a vapor-deposited aluminum or silicon monoxide layer and multi-layer films comprising such materials as polyethylene terephthalate, polyvinyl alcohol, polyvinylidene chloride, ethylene-vinyl alcohol copolymer, etc. in suitable combinations. Among the various materials mentioned above, transparent materials through which the contents of the container can be visually inspected, such as a laminate film carrying a vapor-deposited silicon monoxide layer or a multi-layer film comprising a combination of polyethylene terephthalate, polyvinyl alcohol, polyvinylidene chloride, ethylene-vinyl alcohol copolymer and/or the like, are preferred.

The bicarbonate for use in the present invention includes sodium hydrogen carbonate, potassium hydrogen carbonate, ammonium hydrogen carbonate and other bicarbonates. As representative examples of said bicarbonate-containing powdery pharmaceutical composition may be mentioned various powdery preparations for dialysis use (powdered dialysate preparations for artificial kidney use and powdery preparations for peritoneal dialysis) and antibiotic preparations.

The antibiotics for use as active ingredients of said antibiotic-containing pharmaceutical compositions may be any known antibiotics such as cephalosporins antibiotics, e.g. cefazolin sodium, ceftizoxime sodium, cefotiam hydrochloride, cefmenoxime hydrochloride, cefacetrile sodium, cefamandole sodium, cefaloridine, cefotaxime sodium, cefotetan sodium, cefoperazone sodium, cefsulodin sodium, ceftezole sodium, cefpiramide sodium, cefmetazole sodium, cefuroxime sodium, ceftazidime, etc., penicillin antibiotics such as ampicillin sodium, carbenicillin sodium, sulbenicillin sodium, ticarcillin sodium, cloxacillin sodium, piperacillin sodium, etc., monobactam antibiotics such as carumonam sodium, and carbapenem antibiotics such as imipenem and so on.

In the present invention which comprises introducing carbon dioxide gas into the space between said container accommodating a bicarbonate-containing powdery pharmaceutical composition and said wrapper, disposing a carbon dioxide gas-liberating deoxygenating agent in said space or disposing a desiccant saturated with carbon dioxide gas by way of adsorption in said space, the concentration of carbon dioxide gas in the container can be maintained at the proper level. For stabilizing a hygroscopic pharmaceutical composition, a desiccant can be further disposed in said space to attain a more satisfactory stabilizing effect.

The present invention may also be carried into practice by using a moisture- and gas-impermeable plastic container and filling a powdery pharmaceutical composition, such as a powdered dialysate composition, directly into the container. In this mode, the object of the invention can be accomplished by filling carbon dioxide gas in the container. However, the carbon dioxide gas-liberating deoxygenating agent and the desiccant adsorptively saturated with carbon dioxide gas cannot be disposed in the container because it would result in a direct contact of them with the bicarbonate-containing powdery composition.

Filling of the container with carbon dioxide gas can be carried out by any of the conventional methods. For example, when said wrapper is employed, the space between the wrapper and the plastic container can be filled with carbon dioxide gas or a mixture gas of carbon dioxide and nitrogen. When a container impermeable to moisture and gas is employed, the container may be filled with carbon dioxide gas or said mixture gas in the same manner. In either procedure, it is preferable to evacuate the air from the container beforehand, i.e. preceding said filling with carbon dioxide gas.

The carbon dioxide gas-liberating deoxygenating agent which can be used in the present invention can be any substance having both deoxygenating and carbon dioxide gas-liberating activities but is preferably a substance which is capable of removing oxygen from said space and insuring a high output of carbon dioxide gas. Such deoxygenating agent includes those which contain, as the principal active ingredient, at least one member selected from the group consisting of iron powder; reducing inorganic salts such as dithionites, sulfites, ferrous salts, etc.; polyphenols such as hydroquinone, catechol, etc., reducing polyhydric alcohols such as ascorbic acid, erythorbic acid and their salts. The dithionites absorb oxygen in the presence of water and, at the same time, react with a bicarbonate or carbonate to yield carbon dioxide gas. The agents comprising sodium ascorbate and ferrous sulfate as main ingredients absorb oxygen and generate carbon dioxide gas in the presence of water. Commercial products among such carbon dioxide gas-liberating deoxygenating agents include Ageless G (registered trademark, Mitsubishi Gas Chemical) and Sendo-Hojizai (Keep-Fresh) Type C (Toppan Printing), among others.

The desiccant saturated with carbon dioxide gas for use in the present invention includes silica gel, various aluminum silicates, crystalline hydrated alkali metal or alkaline earth metal aluminosilicates and zeolites which have been saturated with carbon dioxide gas by way of adsorption. To let said desiccant adsorb carbon dioxide gas to saturation, the desiccant is allowed to stand in a carbon dioxide atmosphere at room temperature or a lower temperature, preferably not higher than about 15° C., for several hours. For example, when the commercial product Zeolum (registered trademark) A4 (Tosoh), is subjected to the above procedure, the desired desiccant saturated with carbon dioxide gas is easily obtained. Zeolum (registered trademark) A3RG (Tosoh), which is comparatively low in carbon dioxide adsorption potential, can also be saturated with carbon dioxide gas in the same manner. When the desiccant saturated with carbon dioxide gas is disposed in the space between the plastic container and wrapper, carbon dioxide gas is liberated from the desiccant saturated with carbon dioxide gas so that a carbon dioxide atmosphere is established within the space. Moreover, since such desiccant has a high adsorptive affinity for water vapor than carbon dioxide gas, it adsorbs not only moisture and adherent water from the powdery pharmaceutical composition within the plastic container but, depending on conditions, the water which may be liberated by decomposition of the bicarbonate for some cause or other to release carbon dioxide gas so that the carbon dioxide partial pressure within the container is elevated to inhibit decomposition of the bicarbonate.

It should be understood that when the relative humidity in the container is to be maintained at a level not exceeding 1% at 25° C. in the present invention, zeolites having high dehydrating agents are preferably employed.

In the present invention, a desiccant saturated with carbon dioxide gas and a deoxygenating agent which absorbs oxygen by way of oxidation reaction, such as said iron powder, dithionites, sulfites, ferrous salts, etc., can be used in combination. In this mode, when a moisture-containing self-reacting type deoxygenating agent (e.g. Ageless Z from Mitsubishi Gas Chemical) is used as said deoxygenating agent, the carbon dioxide concentration and moisture level within the container can be adequately maintained without causing degradation of the bicarbonate-containing powdery pharmaceutical composition.

In the present invention, a carbon dioxide gas-liberating deoxygenating agent and a desiccant can be used in combination. In this mode, the use of a moisture-containing carbon dioxide gas-liberating deoxygenating agent is particularly preferred. Thus, when such a moisture-containing carbon dioxide gas-liberating deoxygenating agent is used in combination with a desiccant, the deoxygenating agent releases traces of water and the desiccant is prevented from adsorbing carbon dioxide gas owing to the preferential adsorption of such traces of water so that the carbon dioxide gas in the space is maintained at a suitable concentration level. The use of said carbon dioxide gas-liberating deoxygenating agent is also beneficial when the bicarbonate-containing powdery pharmaceutical composition is a composition susceptible to oxidative decomposition.

Thus, in accordance with the present invention, the bicarbonate-containing powdery pharmaceutical composition can be preserved in a plastic container without aging and degradation and, at the same time, the object of addition of the bicarbonate can be accomplished without compromise.

Figure 1:
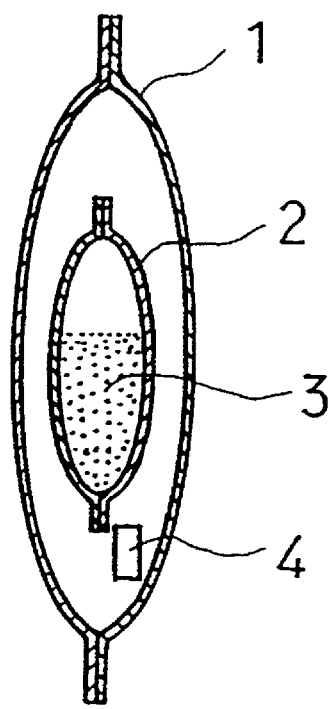
FIG. 1 is a schematic sectional view showing a typical package form of the invention as obtained in Example 1 which appears hereinafter.

In the view, (1) stands for a plastic wrapper, (2) for a plastic container, (3) for a bicarbonate-containing powdery pharmaceutical composition, and (4) for a carbon dioxide gas-liberating deoxygenating agent.

BEST MODE OF PRACTICING THE INVENTION

The following examples are intended to illustrate the invention in further detail. The materials used in the examples are referred to by the following abbreviations.

| L-LDPE | Linear low-density polyethylene |
| --- | --- |
| KPET | Polyvinylidene chloride-coated polyethylene terephthalate |
| PVDC | Polyvinylidene chloride |

Example 1

A bag (175 μm thick, 50×50 mm) made of L-LDPE (density 0.920) was filled with 20 mg of sodium hydrogen carbonate and 100 mg of sodium chloride. Then, this filled bag and one piece of the carbon dioxide gas-liberating oxygenating agent (Ageless G15, Mitsubishi Gas Chemical) were placed in a laminate-film wrapping bag of KPET (15 μm)/PVDC (25 μm)/L-LDPE (30 μm) (sized 70×70 mm), followed by heat sealing to provide a container of the invention as illustrated in FIG. 1. This product is used for a carbon dioxide gas-liberating deoxygenating agent group.

Similarly an L-LDPE bag containing said drugs was prepared and placed in the same wrapping bag as above. This was followed by filling with a mixture gas of 5%, 10% or 20% of carbon dioxide gas and the balance of air and the wrapping bag was heat-sealed. This was used for a carbon dioxide-filled group. As a control, the same L-DPE bag containing the drugs, not packaged in the wrapping bag, was tested. This was used for a control group.

The samples in the above $CO_2$-liberating deoxygenating agent group, $CO_2$ gas-filled group and control group were stored at 40° C. and 75% RH. The samples immediately after manufacture and after storage periods of 1, 2 and 3 months were respectively dissolved in 100 ml of physiological saline and the pH of each solution was measured. The results are shown in Table 1.

TABLE 1

| Sample groups | Immediately after manufacture | Storage at 40° C. and 75% RH | | |
|---|---|---|---|---|
| | | 1 Month | 2 Months | 3 Months |
| $CO_2$ gas-liberating deoxygenator group | 8.02 | 8.05 | 8.02 | 8.03 |
| $CO_2$ gas-filled group | | | | |
| $CO_2$ concentration 5% | 8.02 | 8.05 | 8.07 | 8.04 |
| $CO_2$ concentration 10% | 8.02 | 8.03 | 8.02 | 8.05 |
| $CO_2$ concentration 20% | 8.04 | 8.03 | 8.05 | 8.02 |
| Control | 8.03 | 8.23 | 8.47 | 8.69 |

Each value is the mean of n = 3

It is apparent from Table 1 that the solutions from the carbon dioxide-liberating deoxygenator group and carbon dioxide gas-filled group showed no pH elevation, indicating that the use of a carbon dioxide gas-liberating deoxygenating agent and the procedure of filling with carbon dioxide gas, both according to the invention, arrested decomposition of the bicarbonate in the plastic container.

While a mixed powder of sodium hydrogen carbonate and sodium chloride was used as the bicarbonate-containing powdery pharmaceutical composition in this example, the method described in this example of the invention can be applied with advantage to any other powdery composition comprising a varying type of electrolyte other than sodium chloride in combination with sodium hydrogen carbonate, for example a powdered dialysate composition.

Example 2

A laminate film bag of KPET (15 μm)/PVDC (25 μm)/L-LDPE (30 μm) (sized 90×90 mm) was filled with 20 mg of sodium hydrogen carbonate and 100 mg of sodium chloride. The bag was then filled with a mixture gas of 5%, 10% or 20% of carbon dioxide gas and the balance of air and heat-sealed to provide a package form of the invention.

The above package form was stored at 40° C./75% RH and samples immediately after manufacture and after storage periods of 1, 2 and 3 months were respectively dissolved in 100 ml of physiological saline and the pH of each solution was measured.

As a result, the solution from the above package form was as stable as that in the $CO_2$ gas-filled group of Example 1. Moreover, the method and package form described in this example were suited for powdered dialysate compositions.

Example 3

Using a pharmaceutical composition (hereinafter referred to as Drug A) comprising one gram (potency) of a crystalline powder of cefalexin (hereinafter referred to as CEX), a cephem antibiotic, and 20 mg of sodium hydrogen carbonate, the following experiment was carried out.

Thus, Drug A was filled into a glass vial (⌀26 mm, Nichiden Rika Glass), stoppered with a butyl rubber stopper and clinched with an aluminum band (Sample 1, control).

Then, Drug A was filled into a bag (175 μm thick, 50×50 mm) made of L-LDPE (density 0.920) and the filled bag was placed in a laminate-film wrapping bag of KPET (15 μm)/PVDC (50 μm)/L-LDPE (50 μm) (sized 70×70 mm) and heat-sealed (Sample 2, comparative example). Samples were prepared in the same manner except that 6 g of silica gel (Fuji Gel Industry) was inserted before said heat-sealing (Sample 3, comparative example), 2 g of a zeolite (Zeolum A4, Tosoh) was placed before said heat-sealing (Sample 4, comparative example), 2 g of a zeolite (Zeolum A3RG, Tosoh) previously saturated with carbon dioxide gas was inserted (Sample 5, this invention), 2 g of a zeolite (Zeolum A3RG, Tosoh) and one piece of a $CO_2$ gas-liberating deoxygenating agent (Ageless G20, Mitsubishi Gas Chemical) were inserted (Sample 6, this invention), and 2 g of a zeolite (Zeolum A4, Tosoh) and one piece of a $CO_2$ gas-liberating deoxygenating agent were inserted (Ageless G20, ditto) (Sample 7, this invention).

The above samples were stored at 40° C. and 75% RH.

In a preliminary experiment in which the respective samples were stored at 40° C. and 75% RH, elevations of pH were observed after 2 months of storage at 40° C./75% RH. Based on this result, the samples prior to the beginning of storage and those after 3 months of storage were examined for the pH of Drug A (as dissolved in 100 ml of physiological saline), water content, potency (calculated on the anhydrous basis), carbon dioxide concentration in the bag, and appearance (color).

The results are shown in Table 2.

TABLE 2

| No. | Container | Desiccant | $CO_2$-liberating deoxygenator |
|---|---|---|---|
| 1 | Glass vial + rubber stopper | — | — |
| 2 | Plastic bag + laminate film wrapper | — | — |
| 3 | Plastic bag + laminate film wrapper | Silica gel, 6 g | — |
| 4 | Plastic bag + laminate film wrapper | Zeolum A4, 2 g | — |
| 5 | Plastic bag + laminate film wrapper | Zeolum A3RG*, 2 g | — |
| 6 | Plastic bag + laminate film wrapper | Zeolum A3RG, 2 g | Ageless G20 |
| 7 | Plastic bag + laminate film wrapper | Zeolum A4, 2 g | Ageless G20 |

| Before storage | | | | | |
|---|---|---|---|---|---|
| No. | pH | Moisture content (%) | Potency of antibiotic (μg (potency)/mg) | $CO_2$ concentration (ppm) | Appearance |
| 1 | 7.24 | 4.35 | 994 | 291 | White |
| 2 | 7.28 | 4.27 | 1018 | 275 | White |
| 3 | 7.32 | 4.11 | 1001 | 230 | White |
| 4 | 7.30 | 4.24 | 1031 | 0 | White |
| 5 | 7.31 | 4.18 | 992 | 254 | White |
| 6 | 7.26 | 4.20 | 1007 | 2825 | White |
| 7 | 7.25 | 4.21 | 1012 | 0 | White |

| After 3 months of storage at 40° C./75% RH | | | | | |
|---|---|---|---|---|---|
| No. | pH | Moisture content (%) | Potency of antibiotic (μg (potency)/mg) | $CO_2$ concentration (ppm) | Appearance |
| 1 | 7.26 | 4.34 | 998 | 2141 | White |
| 2 | 6.35 | 5.15 | 723 | 2180 | Pale yellow |
| 3 | 7.80 | 4.15 | 1009 | 824 | White |
| 4 | 8.02 | 4.18 | 1002 | 0 | White |
| 5 | 7.43 | 4.14 | 1015 | 1521 | White |
| 6 | 7.18 | 4.22 | 999 | 9891 | White |
| 7 | 7.23 | 4.15 | 1002 | 7368 | White |

Zeolum A3RG* in Sample No. 5 in Table 2 was previously saturated with carbon dioxide gas.

Referring to the combination of an L-LDPE container and a laminate film wrapper, Sample 2 (comparative example)

which contained neither of the desiccant and carbon dioxide gas-liberating deoxygenating agent was affected by external moisture to show a decrease in potency of the antibiotic and a change in appearance. The pH was also fairly depressed and it was considered attributable to decomposition products of CEX.

Sample 3 (comparative example) which contained a silica gel having no high desiccating power showed no loss of potency or an increase in moisture content because CEX is not so hygroscopic. However, the pH of its solution showed an increase of about 0.5 from the value prior to storage. The cause of this increase is that because the desiccant adsorbed moisture, the sodium hydrogen carbonate was partially decomposed to sodium carbonate.

Sample 4 (comparative example) in which Zeolum A4, a potent desiccant, was used, there was no decrease in potency but because of the marked adsorption of carbon dioxide gas on the desiccant, the pH exceeded 8 at 3 months of storage, an increase of about 0.7. This result suggested that the use of a potent desiccant alone is not effective enough for the stabilization of powdery antibiotic products.

On the other hand, Sample 5, Sample 6 and Sample 7 (all of the invention) showed findings comparable to those of Sample 1 (control) employing the glass vial which is the ordinary container for antibiotics, in potency, moisture level and pH.

Sample 5, in which the low $CO_2$-adsorbing Zeolum A3RG was previously saturated with carbon dioxide gas, showed a lesser change of pH and no remarkable difference in carbon dioxide concentration as compared with Sample 1.

On the other hand, Sample 6 and Sample 7, in which a $CO_2$-liberating deoxygenating agent was employed, showed somewhat higher $CO_2$ concentrations than Sample 1 and Sample 5 but no changes of significance in potency, moisture level and pH.

Thus, the bicarbonate-containing pharmaceutical composition in a plastic container could be well maintained by means of a moisture- and gas-impermeable wrapper, a desiccant and a carbon dioxide gas-liberating deoxygenating agent without causing the aging and degradation of the active ingredient(s) and without inducing the formation of carbonate from bicarbonate.

INDUSTRIAL APPLICABILITY

The method of the present invention for stabilizing a bicarbonate-containing powdery pharmaceutical composition insures an increased carbon dioxide gas concentration in the container, prevents aging and degradation of the drug over a long period of time with great effectiveness and helps accomplish the objectives of incorporation of the bicarbonate, namely the supply of $HCO_3^-$, neutralization of the drug, and assistance in dissolution.

Furthermore, the invention enables the supply of containers for such stabilized bicarbonate-containing powdery pharmaceutical compositions.

We claim:

1. A method of stabilizing a bicarbonate-containing powdery pharmaceutical composition comprising filling the bicarbonate-containing powdery pharmaceutical composition in a moisture- and gas-permeable plastic container, wrapping the so-filled container in a moisture- and gas-impermeable plastic wrapper and carrying out at least one procedure selected from the group consisting of a procedure of introducing carbon dioxide into a space between said container and wrapper, a procedure of introducing a carbon dioxide-liberating deoxygenating agent in said space and a procedure of introducing a desiccant previously saturated with carbon dioxide by way of adsorption in said space.

2. The method defined in claim 1 wherein said carbon dioxide-liberating deoxygenating agent and desiccant are introduced together in the space between said container and wrapper.

3. The method defined in claim 1 wherein said bicarbonate-containing powdery pharmaceutical composition is a powdered dialysate composition.

4. The method defined in claim 1 or 2 wherein said bicarbonate-containing powdery pharmaceutical composition is an antibiotic-containing composition.

5. A method of stabilizing a bicarbonate-containing powdery pharmaceutical composition comprising filling said bicarbonate-containing powdery pharmaceutical composition in a moisture- and gas-impermeable plastic wrapper as a container and filling carbon dioxide gas in said container.

6. The method defined in claim 5 wherein said bicarbonate-containing powdery pharmaceutical composition is a powdered dialysate composition.

7. A package form for insuring a stabilized bicarbonate-containing pharmaceutical composition wherein said package form comprises (1) a moisture- and gas-permeable plastic container accommodating the bicarbonate-containing pharmaceutical composition, (2) a moisture- and gas-impermeable plastic wrapper covering the container and (3) at least one member selected from the group consisting of carbon dioxide, a carbon dioxide-liberating deoxygenating agent and a desiccant previously saturated with carbon dioxide by way of adsorption, said member being introduced in a space between said container and wrapper.

8. The package form defined in claim 7 wherein said carbon dioxide-liberating deoxygenating agent and desiccant are introduced together in the space between said container and wrapper.

9. A packaged bicarbonate-containing powdery pharmaceutical composition comprising a bicarbonate-containing powdery pharmaceutical composition present in a moisture- and gas-impermeable plastic wrapper as a container filled with carbon dioxide.

* * * * *